Figure 1A:
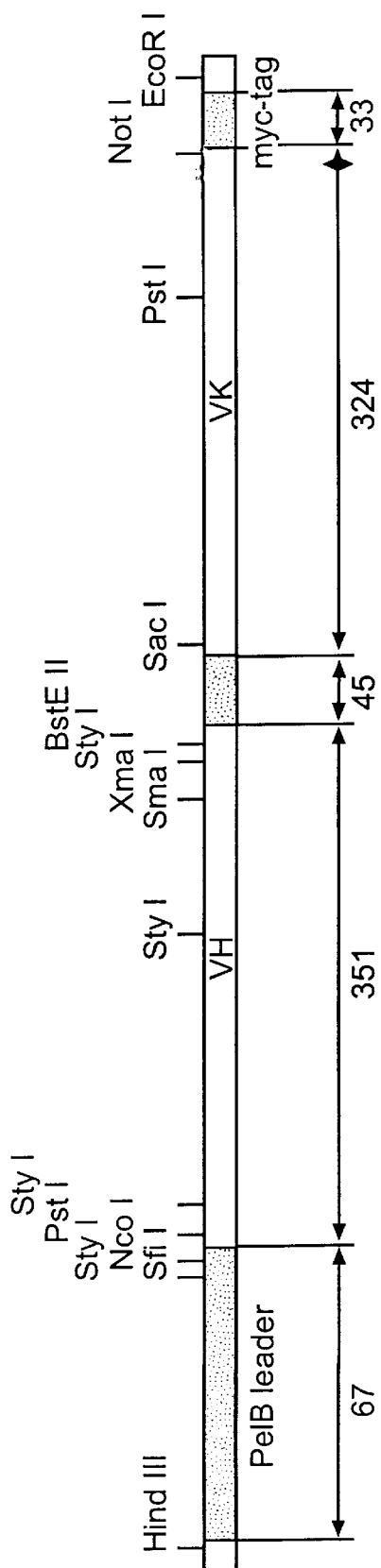

United States Patent [19]
Schweighoffer et al.

[11] Patent Number: 6,159,947
[45] Date of Patent: Dec. 12, 2000

[54] ANTI-RAS INTRACELLULAR BINDING PROTEINS AND USE THEREOF

[75] Inventors: Fabien Schweighoffer, Vincennes; Bruno Tocque, Courbevoie, both of France

[73] Assignee: Aventis Pharma S.A., Antony, France

[21] Appl. No.: 08/564,164

[22] PCT Filed: Jun. 15, 1994

[86] PCT No.: PCT/FR94/00714

§ 371 Date: Dec. 28, 1995

§ 102(e) Date: Dec. 28, 1995

[87] PCT Pub. No.: WO94/29446

PCT Pub. Date: Dec. 22, 1994

[30] Foreign Application Priority Data

Jun. 16, 1993 [FR] France ................................. 93 07241

[51] Int. Cl.$^7$ ..................... A01N 43/04; A61K 31/70; C12N 15/63; C12N 15/00
[52] U.S. Cl. ..................... 514/44; 435/320.1; 435/325; 435/455; 435/69.1; 435/7; 424/93.21; 536/23.1; 536/23.4; 536/23.5; 536/23.53
[58] Field of Search .......................... 536/23.1, 23.4, 536/23.5, 23.53; 435/320.1, 172.3, 325, 455, 69.1, 7; 424/93.2, 93.21; 514/44

[56] References Cited

U.S. PATENT DOCUMENTS 4,946,778  8/1990  Ladner et al. ...................... 435/69.6

FOREIGN PATENT DOCUMENTS

| 0520499 | 12/1992 | European Pat. Off. . |
| 39 15 952 | 6/1990 | Germany . |
| WO 92/05250 | 4/1992 | WIPO . |
| WO 93/07286 | 4/1993 | WIPO . |
| WO 93/12232 | 6/1993 | WIPO . |
| WO 94/02610 | 2/1994 | WIPO . |

OTHER PUBLICATIONS

Werge et al., Cloning and intracellular expression of a monoclonal antibody to the p21ras Protein, FEBS 274(1, 2):193–198 (1990).
Piccioli et al., Neuroantibodies: Molecular cloning of a monoclonal antibody against substance P for expression in the central nervous system, Proc. Natl. Acad. Sci. 88:5611–5615 (1991).
Biocca et al., Expression and targeting of intracellular antibodies in mammalian cells, EMBO Journal 9(1): 101–108 (1990).
Huston et al., Protein engineering of antibody binding sites: Recovery of specific activity in an anti–diogoxin single–chain Fv analogue produced in Excherichia coli, Proc. Natl. Acad. Sci. USA 85:5879–5883 (1988).
Biooca et al., Intracellular Expression of Anti–p21ras Single Chain Fragments Inhibits Melotic Maturation of Xenopus Oocytes, Biochemical & Biophysical Research Commun. 197(2): 422–427 (1993).
Chaudhary et al., Pdeudomonas exotoxin contains a specific sequence at the carboxyl terminus that is required for cytotoxicity, Proc. Natl. Acad. Sci. USA 87: 308–312 (1990).
Benvenisty et al., Direct introduction of genes into rats and expression of the genes, Proc. Natl. Acad. Sci. USA 83: 9551–9555 (1986).
Wang et al., pH–sensitive immunoliposomes mediate target–cell–specific delivery and controlled expression of a foreign gene in mouse, Proc. Natl. Acad. Sci. USA 84:7851–7855 (1987).
Nicolau et al., In vivo expression of rat insulin after intravenous administration of the liposome–entrapped gene for rat insulin I, Proc. Natl. Acad. Sci. USA 80:1068–1072 (1983).
Trono et al., HIV–1 Gag Mutants Can Dominantly Interfere with the Replication of the Wild–Type Virus, Cell 59: 113–120 (1989).
Sullenger et al., Overexpression of TAR Sequences Renders Cells Resistant to Human Immunodeficiency Virus Replication, Cell 63: 601–608 (1990).
Munro et al., A C–Terminal Signal Prevents Secretion of Luminal ER Proteins, Cell 48: 899–907 (1987).
Malim et al., Functional Dissection of the HIV–1 Rev Trans–Activator–Derivation of a Trans–Dominant Repressor of Rev Function, Cell 58:205–214 (1989).
Posner et al., An IgG Human Monoclonal Antibody That Reacts with HIV–1/GP120, Inhibits Virus Binding To Cells, and Neutralizes Infection, The Journal Immunology 146(12):4325–4332 (1991).
Buonocore et al., Prevention of HIV–1 glycoprotein transport by soluble CD4 retained in the endoplasmic reticulum, Nature 345:625–628 (1990).
Haseloff et al., Simple RNA enzymes with new and highly specific endoribonuclease activities, Nature 334:585–591 (1988).
Rosenberg et al., Gene Transfer Into Humans–Immunotherapy of Patients With Advanced Melanoma, Using Tumor–Infiltrating Lymphocytes Modified By Retroviral Gene Transduction, The New England Journal of Medicine 323: 570–578 (1990).
Riechmann et al., Expression of an Antibody Fv Fragment in Myeloma Cells, J. Mol. Biol. 203: 825–828 (1988).
Carlson, A New Means of Inducibly Inactivating a Cellular Protein, Molecular & Cellular Biology 8(6): 2638–2646 (1988).

(List continued on next page.)

*Primary Examiner*—Jasemine Chambers
*Assistant Examiner*—Jill D. Martin
*Attorney, Agent, or Firm*—Finnegan, Henderson, Farabow, Garrett & Dunner, L.L.P.

[57] ABSTRACT

The present invention relates to nucleic acid sequences encoding intracellular binding proteins. More particularly, the nucleic acid comprises a gene coding for an intracellular single chain antibody specific for a ras oncogene under the control of a promoter, the antibody is functional in mammalian cells, and inhibits the transformation of cells that express a ras oncogene.

14 Claims, 2 Drawing Sheets

OTHER PUBLICATIONS

Poznansky et al., Gene Transfer into Human Lymphocytes by a Defective Human Immunodeficiency Virus Type 1 Vector, Journal of Virology 65(1): 532–536 (1991).

Faraji–Shadan et al., A Putative Approach for Gene Therapy Against Human Immunodeficiency Virus (HIV), Medical Hypotheses 32: 81–84 (1990).

Brake et al., Characterization of Murine Monoclonal Antibodies to the tat Protein from Human Immunodeficiency Virus Type 1, Journal of Virology 64(2): 962–965 (1990).

Kaneda et al., Increased Expression of DNA Cointroduced with Nuclear Protein in Adult Rat Liver, Science 243: 375–378 (1989).

Anderson, Prospects for Human Gene Therapy, Science 226: 401–409 (1984).

Selden et al., Implantation of Genetically Engineered Fibroblasts into Mice: Implications for Gene Therapy, Science 236: 714–718 (1987).

Sarver et al., Ribozymes as Potential Anti–HIV–1 Therapeutic Agents, Science 247: 1222–1225 (1990).

Baltimore, Intracellular Immunization, Nature 335:395–396 (1988).

Felgner et al., Gene Therapeutics, Nature 349: 351–354 (1991).

Seetharam et al., Increased Cytotoxic Activity of Pseudomonas Exotoxin and Two Chimeric Toxins Ending in KDEL, The Journal of Biological Chemistry 266(26): 17376–17381 (1991).

Wu et al., Receptor–mediated Gene Delivery and Expression in Vivo, The Journal of Biological Chemistry 263(29): 14621–14624 (1988).

Schultz et al., Hydroxylamine–Stable Covalent Linkage of Myristic Acid in Goa, A Guanine Nucleotide–Binding Protein of Bovine Brain, Biochemical & Biophysical Rsch. Commn. 146(3): 1234–1239 (1987).

Siomi et al., Sequence Requirements for Nucleolar Localization of Human T Cell Leukemia Virus Type I pX protein, Which Regulates Viral RNA Processing, Cell 55:197–209 (1988).

Spence et al., Affinity Purification and Characterization of Anti–Tac(Fv)–C3–PE38KDEL: A Highly Potent Cytotoxic Agent Specific to Cells Bearing IL–2 Receptors, Bioconjugate Chem. 4:63–68 (1993).

Kreitman et al., Single–Chain Immunotoxin Fusions between Anti–Tac and Pseudomonas Exotoxin: Relative Importance of the Two Toxin Disulfide Bonds, Bioconjugate Chem. 4: 112–120 (1993).

Norley et al., Vaccination against HIV, Immunobion 184: 193–207 (1992).

van der Krol et al., Modulation of Eukaryotic Gene Expression by Complementary RNA or DNA Sequences, BioTechniques 6(10: 958–976 (1988).

Russell et al., Retroviral Vectors Displaying Functional Antibody Fragments, Nucleic Acids Research, 21:5, 1081–1085 (1993).

Rodwell, Engineering Monoclonal Antibodies, Nature, 342:6245, 99–100, (1989).

Liu et al., Cancer Research, vol. 54, pp. 3662–3667, Jul. 15, 1994.

Clayman et al., Cancer Research, vol. 55, pp. 1–6, Jan. 1, 1995.

Clayman et al., Arch. Otolaryngol. Head Neck Surg., vol. 122, pp. 489–493, May. 1996.

Clayman et al., Journal of Clinical Oncology, vol. 16, pp. 2221–2232, Jun. 1998.

El–Naggar etal., Society for Biological Therapy: Annual Meeting, Sep. 1996.

Orkin et al., "Report and Recommendations of the Panel to Assess the NIH Investment in Research on Gene Therapy.", Dec. 7, 1995.

Eck and Wilson, Goodman & Gilman's The Pharmacological Basis of Therapeutics, "Gene–Based Therapy", Ninth Edition: McGraw–Hill, chapter 5, pp. 77–101, 1995.

Hanania et al., American Journal of Medicine, vol. 99, pp. 537–552, Nov. 1995.

Cochet et al., Cancer Research, vol. 58, pp. 1170–1176, 1998.

Richardson et al., Trends in Biotechnology, vol. 13, pp. 306–310, 1995.

Shirasawa et al., Science, vol. 260, pp. 85–88, Abstract only, Apr. 2, 1993.

Levrero et al (1991) Gene 101:195–202.

Orlandi et al (1989) Proc. Natl. Acad. Sci. USA 86:3833–3837.

Furth et al (1982) J. Virol. 43:294–304.

Gazitt et al (1992) J. Immunological Methods 148:159–169.

Milner et al (1986) Virology 154:21–30.

Duchesne et al (1993) Science 259:525–528.

Marshall, E (1995) Science 269:1050–1055.

Miller et al (1995) FASEB J 9:190–199.

Crystal, R.G (1995) Science 270:404–410.

ANTI-RAS INTRACELLULAR BINDING PROTEINS AND USE THEREOF

The present invention relates to nucleic acid sequences, to vectors containing them and to their therapeutic uses, in particular in gene therapy. More especially, the present invention relates to nucleic acid sequences comprising a gene coding for an intra-cellular binding protein (IBP) and to their use in gene therapy, where appropriate incorporated in suitable expression vectors.

Gene therapy consists in correcting a deficiency or abnormality (mutation, aberrant expression, and the like) by introduction of genetic information into the affected cell or organ. This genetic information may be introduced either in vitro into a cell extracted from the organ, the modified cell then being reintroduced into the body, or directly in vivo into the appropriate tissue. In this connection, different techniques of transfection and of gene transfer have been described in the literature (see Roemer and Friedman, Eur. J. Biochem. 208 (1992) 211). To date, the approaches proposed in the prior art for gene therapy consist in transferring genes coding for active polypeptides involved in genetic disorders (hormones, growth factors, and the like), antisense genes, or antigenic peptides for the production of vaccines. The present invention relates to a new approach to gene therapy, consisting in transferring and expressing in a target cell (or tissue) an intracellular peptide capable of interacting with cell components and thus of interfering with cell functions. The present invention is based more especially on the demonstration that it is possible to express in vivo modified antibodies which remain in the intracellular compartment and which can control certain cell functions. The invention is also based on the demonstration that it is possible to clone DNA sequences coding for such intracellular antibodies into vectors, in particular viral vectors, for use in gene therapy.

The use of antibodies in human therapy makes it possible, in general, to target and neutralize circulating biological complexes and/or those which are localized at the cell surface, by bringing about a cascade of events conducted by the immune system which leads to their removal. However, in many cases, including cancers or diseases due, for example, to viruses, this approach is fruitless since the antigen responsible for the deregulation of the affected cells is inaccessible to the injected antibodies. The present invention affords a new, especially advantageous therapeutic approach, consisting in causing antibodies or therapeutic agents whose binding to their epitope decreases and/or abolishes the deregulation to be produced continuously and intracellularly.

The possibility of recombinant expression of antibodies has already been described in the literature. Thus, Patent EP 88,994 describes the in vitro expression and purification of heavy or light-chain variable regions of antibodies. Likewise, U.S. Pat. No. 4,946,778 describes the in vitro expression of DNA sequences coding for modified antibodies composed of heavy- and light-chain variable regions of an antibody linked via a linker. However, the antibodies described in this patent are inactive, and generally synthesized in the form of insoluble inclusion bodies. The antibodies must hence be purified and then subjected to chemical treatments (denaturation, renaturations, and the like) in order to recover an activity. The present invention demonstrates the possibility of using such DNA sequences for the expression of active intracellular antibodies directly in vivo. The present invention thus demonstrates the possibility of using such DNA sequences coding for intracellular antibodies, under the control of regions permitting their expression in mammalian cells, for gene therapy, in particular in man. This new approach hence makes it possible to target cell components which are not accessible by traditional vaccination methods. Furthermore, this approach does not involve the development of an immune response, but acts intracellularly.

A first subject of the invention hence lies in a nucleic acid sequence comprising a gene coding for an intracellular binding protein (IBP) under the control of regions permitting its expression in mammalian cells.

The invention also relates to vectors containing a nucleic acid sequence as defined above. More especially, the vectors of the invention are of viral origin, such as retroviruses, adenoviruses, adeno-associated viruses, herpesvirus, vaccinia virus, HSV virus, and the like.

The invention also relates to the use of these nucleic acid sequences or these vectors for the preparation of pharmaceutical compositions intended for the surgical and/or therapeutic treatment of the human or animal body. It also relates to any pharmaceutical composition comprising a vector, in particular a viral vector, or a nucleic acid sequence as are defined above.

For the purpose of the present invention, the term intracellular binding protein (IBP) denotes any protein or protein fragment capable of recognizing a component of the cell in which it is expressed, and of interacting selectively with, and with affinity for, this component. The interactions may be covalent or non-covalent chemical interactions. The interaction with the cell component (proteins, lipids, amino acids, mRNA, tRNA, rRNA, DNA, and the like) makes it possible to act on a cell function in which the said component is involved, and thus to control (stimulate, slow down, inhibit) this function.

Preferably, the IBPs according to the invention consist of molecules derived from antibodies or having binding properties comparable to those of an antibody. In particular, they are proteins having sufficient selectivity and affinity to permit an in vivo interaction having a neutralizing effect on the antigen. These molecules are designated hereinafter intracellular antibodies, on account of their properties and their localization.

Antibodies, molecules of the immunoglobulin superfamily, are synthesized naturally (essentially by B lymphocytes) in the form of secreted proteins. They are hence released into the extracellular compartments (circulatory system) where they exert their activity (recognition of and binding to non-self antigens). It has now been shown that it is possible to express in vivo modified genes coding for intracellular antibodies, without affecting the specificity and affinity properties of the antibodies. The nucleic acid sequences according to the invention, which code for intracellular antibodies, hence comprise an antibody gene modified so that the antibody is not secreted. In particular, the gene for the antibody is generally modified by deletion or mutation of the sequences responsible for its secretion. The IBPs according to the invention can, in particular, consist of antibody fragments, and for example of Fab or F(ab)'2 fragments which carry the antigen binding domains. The use of this type of intracellular antibody involves, however, the expression of a nucleic acid sequence comprising several genes coding respectively for the heavy and light regions of these fragments, and it also involves these chains being correctly assembled in vivo. For this reason, an especially advantageous form of intracellular antibodies which are usable in the context of the invention consists of a peptide corresponding to the binding site of the light-chain variable region of an antibody linked via a peptide linker to a peptide corresponding to the binding site of the heavy-chain variable region of an antibody. The use of this type of intracellular antibody, designated ScFv, is advantageous since they are expressed by a single gene. The construction of nucleic acid sequences coding for such modified antibodies according to the invention is illustrated in the examples.

Moreover, the nucleic acid sequences coding for the intracellular antibodies according to the invention can also be modified chemically, enzymatically or genetically for the purpose of generating stabilized and/or multifunctional intracellular antibodies, and/or which are of reduced size, and/or with the aim of promoting their localization in one or other intracellular compartment. Thus, the nucleic acid sequences of the invention can comprise sequences coding for nuclear localization peptides (NLS). In particular, it is possible to fuse the sequences of the invention with the sequence coding for the NLS of SV40 virus, the peptide sequence of which is as follows: MPKKKRK (SEQ ID NO: 13) (Kalderon et al., Cell 39 (1984) 499).

As mentioned above, the nucleic acid sequences according to the invention comprise sequences permitting expression of the gene or genes coding for IBPs in mammalian cells. Generally, the IBP genes are hence placed under the control of transcription and translation promoter regions which are functional in the mammalian cell in which expression is sought. These can be sequences which are homologous with respect to the said cell, that is to say sequences naturally responsible for gene expression in the said cell. They can also be sequences of different origin, that is to say sequences responsible for the expression of proteins in other cell types, sequences responsible for antibody expression under natural conditions, viral expression sequences, for example present in a vector in which the sequences of the invention are incorporated, or alternatively synthetic or semi-synthetic sequences.

As regards use for man, many functional promoters have been described in the literature, such as, for example, the CMV, SV40, Ela, MLP, LTR, and the like, viral promoters. Cellular promoters such as, for example, the promoter of the villin gene are useful since they permit a specific tissue expression (limited to the intestine in the case of villin).

Moreover, the expression sequences can also be modified, for example, in order to adapt them to expression in a particular type of vector or of cell, to reduce their size, to increase their transcription promoter activity, to generate inducible promoters, improve their level of regulation or alternatively change the nature of their regulation. Such modifications may be performed, for example, by in vitro mutagenesis, by introduction of additional control elements or of synthetic sequences or by deletions or substitutions of novel control elements. It can be especially advantageous to use tissue-specific promoters in order to targets the expression of the IBP in one type of tissue only.

Moreover, when the nucleic acid sequence does not contain an expression sequence, the latter may be incorporated in an expression vector, downstream of such a sequence.

To prepare a vector according to the invention, in a first step, a cell function, for example one involved in or responsible for a pathology, on which it is desired to act should be identified. A suitable cell component involved in this function should then be identified, and the IBP which appears best suited to this component (antibody, derivatives, and the like) on the basis of its localization, its role, its nature, and the like, should thereafter be determined. When the IBP has been selected, a corresponding nucleic acid sequence may be obtained by molecular biology techniques (chemical synthesis, cloning, enzymatic modification, and the like) and inserted into a suitable vector according to the methodology described in the examples.

Another subject of the invention relates to pharmaceutical compositions comprising at least one nucleic acid sequence or one vector as are defined above.

The sequences of the invention may be used as they are, for example after injection into a human or animal, to induce the intracellular expression of an IBP for the purpose of affecting a particular cell function. In particular, they may be injected in the form of naked DNA according to the technique described in Application WO 90/11,092. They may also be administered in complexed form, for example with DEAE-dextran (Pagano et al., J. Virol. 1 (1967) 891), with nuclear proteins (Kaneda et al., Science 243 (1989) 375), with lipids (Felgner et al., PNAS 84 (1987) 7413), in the form of liposomes (Fraley et al., J. Biol. Chem. 255 (1980) 10431), and the like.

In a preferred embodiment of the invention, the nucleic acid sequences as defined above are incorporated in a vector. The use of such vectors makes it possible, in effect, to promote entry into cells, to enhance resistance to enzymes and to increase intra-cellular stability and expression levels. The vectors of the invention can equally well be plasmid vectors or viral vectors. However, it is preferable to use a viral vector.

In a preferred embodiment, the invention hence relates to nucleic acid sequences as defined above incorporated in a viral vector. The invention also relates to any recombinant virus comprising, inserted into its genome, at least one nucleic acid sequence coding for an IBP.

As mentioned above, different viruses are capable of being used as vectors for the in vivo transfer and expression of genes according to the invention. By way of example, retroviruses (RSV, HMS, MMS, and the like), HSV virus, adeno-associated viruses, adenoviruses, vaccinia virus, and the like, may be mentioned.

Advantageously, the recombinant virus according to the invention is a defective virus. The term "defective virus" denotes a virus incapable of replicating in the target cell. In general, the genome of the defective viruses used in the context of the present invention hence lacks at least the sequences needed for replication of the said virus in the infected cell. These regions may be either removed (completely or partially), or rendered non-functional, or substituted by other sequences and in particular by the nucleic acid sequences of the invention. Preferably, the defective virus nevertheless retains the sequences of its genome which are needed for encapsidation of the viral particles.

Defective recombinant viruses derived from retroviruses, from adeno-associated viruses, from HSV virus (herpes simplex virus) or from adenoviruses have already been described in the literature [Roemer and Friedmann, Eur. J. Biochem. 208 (1992) 211; Dobson et al., Neuron 5 (1990) 353; Chiocca et al., New Biol. 2 (1990) 739; Miyanohara et al., New Biol. 4 (1992) 238; WO91/18,088; Akli et al., Nature Genetics 3 (1993) 224; Stratford-Perricaudet et al., Human Gene Therapy 1 (1990) 241; EP 185,573, Levrero et al., Gene 101 (1991) 195; EP 243,204)].

It is especially advantageous to use the nucleic acid sequences of the invention in a form incorporated in a defective recombinant adenovirus.

There are, in effect, different serotypes of adenovirus, the structure and properties of which vary somewhat, but which are not pathogenic in man, and in particular non-immunosuppressed subjects. Moreover, these viruses do not integrate in the genome of the cells they infect, and can incorporate large fragments of exogenous DNA. Among the different serotypes, it is preferable to use, in the context of the present invention, adenoviruses type 2 or 5 (Ad 2 or Ad 5). In the case of Ad 5 adenoviruses, the sequences needed for replication are the E1A and E1B regions.

Moreover, the small size of the genes coding for the intracellular antibodies according to the invention makes it possible advantageously to incorporate simultaneously, in the same vector, several genes coding for intracellular antibodies directed against different regions of one or more targeted cell components. A particular embodiment of the invention hence consists of a vector, in particular a viral vector, comprising at least two nucleic acid sequences coding for intracellular binding proteins directed against different epitopes.

The defective recombinant viruses of the invention may be prepared by homologous recombination between a defective virus and a plasmid carrying, inter alia, the nucleic acid sequence as defined above (Levrero et al., Gene 101 (1991) 195; Graham, EMBO J. 3(12) (1984) 2917). Homologous recombination takes place after cotransfection of the said virus and said plasmid into a suitable cell line. The cell line used should preferably (i) be transformable by the said elements, and (ii) contain the sequences capable of complementing the portion of the defective virus genome, preferably in integrated form in order to avoid risks of recombination. By way of example of a line which is usable for the preparation of defective recombinant adenoviruses, the human embryonic kidney line 293 (Graham et al., J. Gen. Virol. 36 (1977) 59), which contains, in particular, integrated in its genome, the left-hand portion of the genome of an Ad5 adenovirus (12%), may be mentioned. By way of example of a line which is usable for the preparation of defective recombinant retroviruses, the CRIP line (Danos and Mulligan, PNAS 85 (1988) 6460) may be mentioned.

The viruses which have multiplied are then recovered and purified according to traditional molecular biology techniques.

The present invention hence also relates to a pharmaceutical composition comprising at least one defective recombinant virus as defined above.

The pharmaceutical compositions of the invention may be formulated for the purpose of topical, oral, parenteral, intranasal, intravenous, intramuscular, subcutaneous, intraocular, and the like, administration.

Preferably, the pharmaceutical compositions contain pharmaceutically acceptable vehicles for an injectable formulation. These can be, in particular, sterile, isotonic saline solutions (monosodium or disodium phosphate, sodium, potassium, calcium or magnesium chloride, and the like, or mixtures of such salts), or dry, in particular lyophilized, compositions which, on addition, as appropriate, of sterilized water or of physiological saline, enable injectable solutions to be formed.

The doses of nucleic acids (sequence or vector) used for the administration can be adjusted in accordance with different parameters, and in particular in accordance with the mode of administration used, the pathology in question, the gene to be expressed or the desired treatment period. Generally speaking, in the case of the recombinant viruses according to the invention, these are formulated and administered in the form of doses of between $10^4$ and $10^{14}$ pfu/ml, and preferably $10^6$ to $10^{10}$ pfu/ml. The term pfu (plaque forming unit) corresponds to the infectious power of a solution of virus, and is determined by infection of a suitable cell culture and measurement, generally after 48 hours, of the number of infected cell plaques. The techniques of determination of the pfu titre of a viral solution are well documented in the literature.

The subject of the invention is also any recombinant cell comprising a nucleic acid sequence as defined above.

The sequences of the invention, where appropriate incorporated in vectors, and the pharmaceutical compositions containing them, may be used for the treatment of many pathologies. They may hence be used for the transfer and expression of genes in vivo in any type of tissue. The treatment can, moreover, be targeted in accordance with the pathology to be treated (transfer to a particular tissue can, in particular, be determined by the choice of a vector, and expression by the choice of a particular promoter). The sequences or vectors of the invention are advantageously used for the production in man or animals, in vivo and intracellularly, of proteins capable of acting specifically on various cell functions such as cell proliferation, synthesis of metabolites, protein synthesis, DNA replication and/or transcription, and the like. The present invention thus makes it possible to treat specifically, locally and effectively many cell dysfunctions at the origin of or resulting from different pathologies, and especially cancers, viral or bacterial diseases or, more generally, any pathology in which a cellular mediator can be identified.

Use for the treatment of pathologies linked to cell proliferation

In an especially advantageous embodiment, the nucleic acid sequences of the invention comprise genes coding for IBPs capable of interacting and interfering with the activity of factors involved in cell proliferation. Cell proliferation involves a multitude of factors such as membrane receptors (G proteins), oncogenes, enzymes (protein kinases, farnesyl transferases, phospholipases, and the like), nucleosides (ATP, AMP, GDP, GTP, and the like), activation factors [guanosine exchange factors (GRF, GAP, and the like), transcriptional factors, and the like], and the like. The intracellular expression of IBPs according to the invention capable of binding and neutralizing such factors enables the process of cell proliferation to be controlled. This is especially advantageous in situations in which cell proliferation eludes the natural regulatory mechanisms, leading, for example, to the appearance of tumours. Many factors (products of oncogenic genes and factors involved in the signalling of the effect of these products) have, in effect, been associated with these phenomena of deregulation of cell proliferation. Thus, 90% of adenocarcinomas of the pancreas possess a Ki-ras oncogene mutated on the twelfth codon (Almoguera et al., Cell 53 (1988) 549). Likewise, the presence of a mutated ras gene has been detected in adenocarcinomas of the colon and cancers of the thyroid (50%), or in carcinomas of the lung and myeloid leukaemias (30%, Bos, J. L. Cancer Res. 49 (1989) 4682). Many other oncogenes have now been identified (myc, fos, jun, ras, myb, erb, and the like), mutated forms of which appear to be responsible for a deregulation of cell proliferation.

The expression of IBPs capable of binding these cell factors (preferably their oncogenic form), and hence of slowing down or inhibiting their effects, affords the possibility of a new therapeutic approach to cancer.

In an especially advantageous embodiment, the present invention relates to vectors containing nucleic acid sequences comprising a gene coding for an intracellular antibody capable of interacting with the expression product of an oncogene or with a factor participating in the pathway of signalling of an oncogene.

Among target oncogenes, the ras, fos, jun, myc, myb and erb oncogenes may be mentioned for the purpose of the invention.

Among factors participating in the pathway of signalling of an oncogene, membrane receptors, which may be targeted at the level of their intracellular domains [G proteins, kinases (for example tyrosine kinase), phosphorylases, farnesyl transferases], nucleoside exchange factors (GAP, GRF, and the like, factors), and the like, may be mentioned in particular.

More preferably, the present invention relates to vectors, in particular of viral origin, containing a nucleic acid sequence coding for an intra-cellular antibody directed against an oncogene or a factor participating in the pathway of signalling of an oncogene, consisting of a peptide corresponding to the binding site of the light-chain variable region of an antibody linked via a peptide linker to a peptide corresponding to the binding site of the heavy-chain variable region of an antibody.

More especially, the invention relates to defective recombinant viruses expressing an intra-cellular antibody directed against a factor of the ras-dependent signalling pathway.

As shown in the examples, the expression of intracellular anti-p21 (expression product of the ras gene), anti-GAP or anti-p53 antibodies enables the transforming phenotype of a cancer cell to be reverted.

Use for the treatment of viral pathologies

The nucleic acid sequences according to the invention can also be sequences coding for intra-cellular antibodies capable of interacting with the infectious cycle of a pathogenic virus (HIV, papillomavirus, and the like).

More especially, in the case of HIV virus, the antiviral agents at present available or in protocols of advanced clinical phases do not enable the virus to be blocked in its multiplication, but merely make it possible to slow down the progression of the disease. One of the main reasons for this lies in the appearance of strains resistant to these antiviral agents. The development of an effective vaccination also runs into many obstacles: the genetic variability of HIV makes it impossible to define a stable antigenic structure to give rise to a humoral or cellular immunological response against the different existing strains. As in the case of antiviral agents where the virus withstands a selection pressure by the expedient of point mutations, in the vaccination trials attempted to date, HIV appears to elude the immune system.

The present invention constitutes a new approach for the treatment of HIV infection, consisting in blocking the virus during its replicative cycle by expression of IBPs, and in particular of intracellular antibodies. The present invention makes it possible, in particular, to circumvent the problem of genetic variability of the virus, in contrast to the vaccinal and antiviral approaches. In the case of traditional vaccination, the immune responses detected mainly take place against variable regions. In contrast, the use of intracellular antibodies according to the invention enables an epitope to be chosen which is not only conserved but also essential to the function of a viral protein. Preferably, the intracellular antibody is directed against an epitope of sufficient size to prevent the virus withstanding and adapting by the expedient of point mutations. Moreover, the small size of the gene coding for the intracellular antibody according to the invention advantageously enables several regions (of only one or of several proteins) to be targeted from the same gene therapy vector.

The two main regulatory proteins of the virus, tat and rev, are targets of primary importance for implementing the present invention. In effect, these two proteins are essential for viral replication. Furthermore, the expression of antisense messenger RNAs or of ribozymes targeting the tat or rev messenger RNA prevents viral replication. The mechanism of action of these proteins is relatively well documented: tat is a transcription transactivation factor, while rev provides for transition between the early and late phases of the replicative cycle. These two proteins exert their activity by binding to the viral messenger RNAs, and the peptide region needed for this binding, which is essential for their function, is relatively well delimited. In addition, it has been shown that overexpression of their site of binding to RNA (TAR region for tat and RRE region for rev) inhibits their function regarding viral expression.

Under these conditions, an especially advantageous embodiment of the invention lies in the use of a DNA sequence coding for an intracellular antibody directed against the tat or rev proteins and capable of neutralizing their activity. Advantageously, such antibodies are directed against the region of tat or rev responsible for their binding to RNA.

Intracellular antibodies according to the invention directed against these epitopes may be prepared according to the methodology described in the examples. In particular, as regards anti-tat antibody, this may be obtained by genetic modification from T-B monoclonal antibody (12) (Hybridolab).

Another important target protein in HIV replication whose function may be readily inhibited by an intracellular antibody is the nucleocapsid protein NCP7. In effect, this protein plays an important part in reverse transcription (early phase), in integration and in a late but nevertheless important phase: encapsidation. This multifunctionality is explained by the fact that it has an enzymatically active structural role. It has been described as a hybridase which is considered to permit the complexing of viral nucleic acids: RNA/DNA and DNA/DNA during reverse transcription, as well as RNA/RNA and RNA/tRNA-lys3 during encapsidation. NCP7 appears to be essential for the production of infectious viruses.

The cytoplasmic expression by gene therapy of intracellular antibodies directed against NCP7, inhibiting its function in the dimerization of the viral RNAs and in encapsidation, constitutes another particular embodiment of the invention.

Intracellular antibodies according to the invention directed against neutralizing epitopes of this protein may be prepared according to methodology described in the examples.

Other viral components can also form the subject of a gene therapy according to the invention, and in particular: the CD4 molecule binding site (for example the envelope glycoprotein (gp120/41)), the envelope multimerization region, the gp120/gp41 cleavage site, the protease, the integrase and, more generally, any viral protein. These domains are not generally accessible when the envelope is in native form. For this reason, they are very feebly immunogenic and a vaccination employing them is impossible. The present invention enables these viral components to be targeted, and thus possesses much greater therapeutic potential. In addition, as mentioned above, the small size of the genes coding for the intracellular antibody according to the invention advantageously makes it possible to express simultaneously, in the same vector, several intracellular antibodies directed against different regions of one or more of these targets.

The nucleic acid sequences according to the invention can also be sequences coding for IBPs capable of interacting and interfering with the activity of factors involved in the synthesis of metabolites, in protein synthesis or alternatively in DNA replication and/or transcription.

The present invention will be described more completely by means of the examples which follow, which are to be considered to be illustrative and non-limiting.

Legend to the figures

Figure 1B:
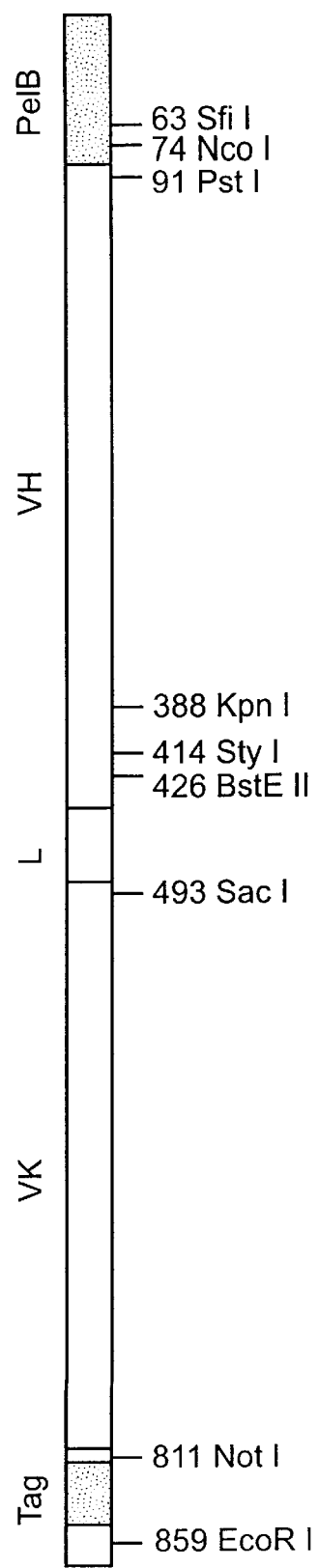
Figure 1C:
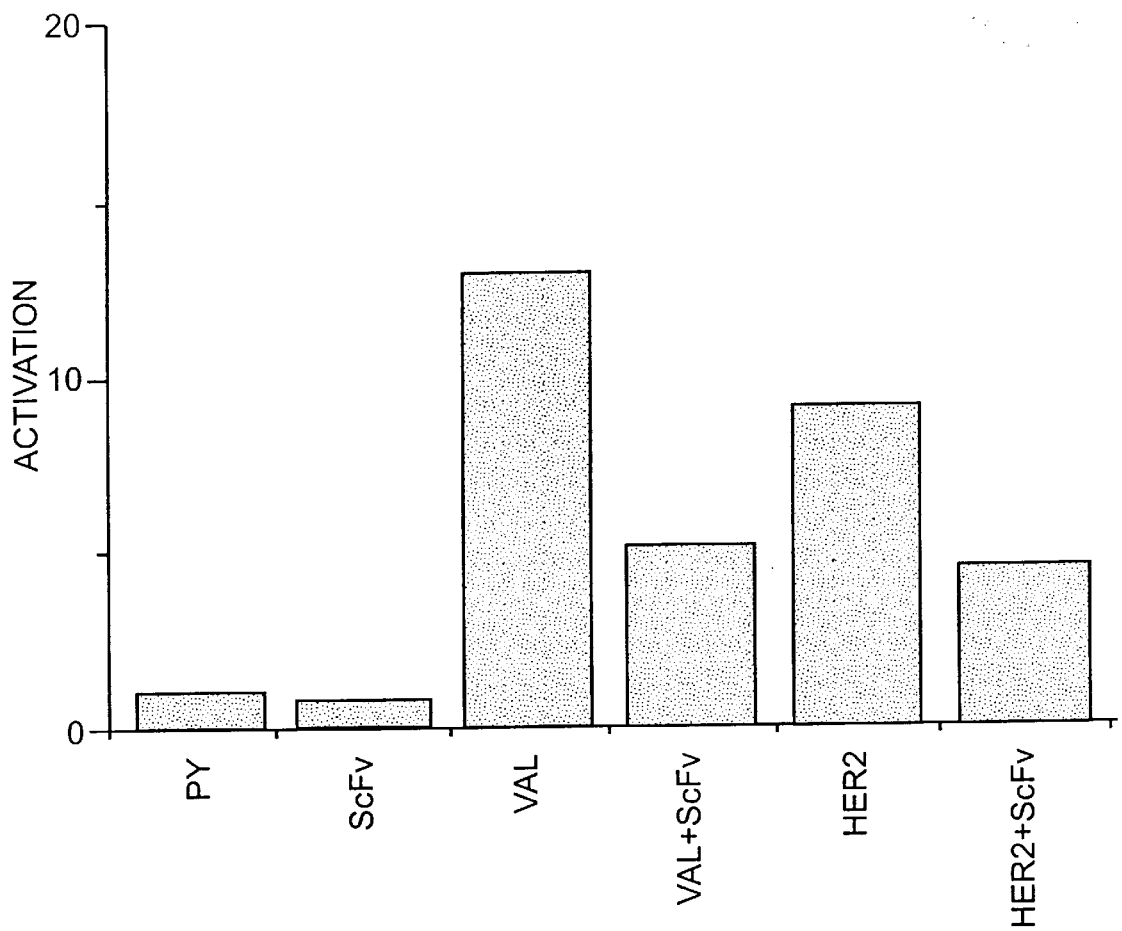

FIG. 1A–C: (A) Restriction map of ScFv-ras. (B) Restriction map of ScFv-Gap. (C) Neutralizing effect of the transient expression of an intracellular antibody of the invention on the transforming power of a ras or Her2 oncogene. Py=control cells; ScFv=cells transected with plasmid psv2.ScFv.ras alone, VAL=cells transected with the vector expressing Ha-ras Val12 oncogenic ras; VAL+ScFv= cells cotransected with plasmid psv2.ScFv.ras and Ha-ras Val12; HER2=cells transected with the vector expressing oncogenic Her2; HER2+ScFv=cells cotransected with plasmid psv2.ScFv.ras and with Her2.

General molecular biology techniques

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, protein extraction with phenol or phenol/chloroform, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

Plasmids of the pBR322 and pUC type and phages of the M13 series are of commercial origin (Bethesda Research Laboratories).

For ligation, the DNA fragments may be separated according to their size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling in of 5' protruding ends may be performed with the Klenow fragment of *E. coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Mutagenesis directed in vitro by synthetic oligodeoxynucleotides may be performed according to the method developed by Taylor et al. [Nucleic Acids Res. 13 (1985) 8749–8764] using the kit distributed by Amersham.

The enzymatic amplification of DNA fragments by the so-called PCR [Polymerase-catalyzed Chain Reaction, Saiki R. K. et al., Science 230 (1985) 1350–1354; Mullis K. B. and Faloona F. A., Meth. Enzym. 155 (1987) 335–350] technique may be performed using a "DNA thermal cycler" (Perkin Elmer Cetus) according to the manufacturer's specifications.

Verification of the nucleotide sequences may be performed by the method developed by Sanger et al. [Proc. Natl. Acad. Sci. USA, 74 (1977) 5463–5467] using the kit distributed by Amersham.

EXAMPLE 1

Cloning and Expression of a DNA Sequence Coding for an Intracellular Anti-ras Antibody This example describes the cloning and expression of a nucleic acid sequence coding for an intracellular binding protein reproducing the properties of Y13-259 monoclonal antibody. Y13-259 antibody is directed against Ras proteins (ref. ATCC CRL 1742) (J. Virol. 43, 294–304, 1982), and is a neutralizing antibody against the function of the oncogenic Ras proteins when injected into cells [Smith et al., (1986) Nature, 320, 540–543; Kung et al., Exp. Cell. Res. (1986) 162, 363–371].

1.1. Preparation of the DNA sequence

A DNA sequence coding for an intracellular antibody (ScFv fragment) was prepared according to the technique described in U.S. Pat. No. 4,946,778. This sequence was then placed under-the control of a promoter which is functional in mammalian cells.

Poly(A) RNAs are isolated from a cell culture of the hybridoma which secretes Y13-259 antibody according to the technique described by Chirguin S. H. et al. [Biochemistry 18, 5294 (1979)]. These RNAs are used for a reverse transcription reaction using primers composed of random hexanucleotides. The cDNAs obtained serve as a template for two PCR reactions:

one intended for amplifying the heavy-chain variable fragment (VH) of Y13-259 with primers specific for murine VH regions, the second enabling the VL fragment to be obtained using a mixture of 10 primers derived from murine sequences.

Two fragments of 340 bp and 325 bp are thereby obtained and then assembled by means of a linker which permits a correct positioning of the VH cDNA at the 5' end of that of VL. This linker codes for 15 amino acids composed of three repeats of the unit $(Gly)_4Ser$ [Orlandi, R. et al., Proc. Natl. Acad. Sci. USA, 86, 3833–3837 (1979)]. The sequence of the intracellular antibody is presented in SEQ ID Nos. 1 & 2 (residues 28 to 270). This sequence endows the VH-VL fusion with enough degrees of freedom to permit their assembly in a parallel orientation and to provide for a correct affinity for the antigen.

The VH-linker-VL fused nucleic acid sequence is then inserted into a phagemid which permits expression of the intracellular antibody (ScFv fragment) at the surface of an M13 phage (FIG. 1A). This expression readily permits identification and selection of the intracellular antibodies which correctly recognize the antigen.

1.2. Functional evaluation of the modified intracellular antibody

The DNA sequence which codes for the modified intracellular anti-Ras antibody (VH-linker-VL) is isolated from the phagemid by restriction, and then inserted into the vector sv2 under the control of the enhancer-early promoter system of SV40 (Schweighoffer et al., Science, 256, 825–827, 1992) in order to test its capacity to antagonize the effects of an oncogenic Ras. The plasmid thereby obtained is designated psv2.ScFv.ras. The functional evaluation was performed according to several tests:

a) Transient transfection in mammalian cells

For evaluation by transient transfection in mammalian cells, plasmid psv2.ScFv.ras was cotransfected into NIH 3T3 cells according to the protocol described in Schweighoffer et al. [Science, 256, 825–827 (1992)] with a vector which permits the expression of a Ha-ras Val 12 gene. The activation state of the signalling pathway under study was recorded by measuring the enzymatic activity obtained from the chloramphenicol acetyltransferase (CAT) reporter gene placed under the control of a promoter containing nucleotide elements responding in trans to the action of Ras (RRE), which were also cotransfected: these RRE elements consist of a polyoma TK hybrid promoter-enhancer (Wasylyk et al., EMBO, J. 7, 2475, 1988).

The results obtained are presented in FIG. 1C. The analysis of the CAT activities obtained demonstrates the capacity of the modified intracellular antibody, prepared from Y13-259 antibody, to antagonize the activity of the oncogenic Ras.

Plasmid psv2.ScFv.ras cotransfected with a plasmid permitting the expression of an oncogene endowed with tyrosine kinase activity, the HER2 (human epidermal growth factor type II) oncogene, also blocks its activity on the test "CAT" plasmid (FIG. 1).

b) Formation of foci of transformed cells:

Cancer cells have the property of forming foci of transformation, and in particular NIH 3T3 fibroblasts expressing an oncogenic Ras (Barlat et al., Oncogene (1993), B, 215–218).

NIH 3T3 cells are cultured as in the previous test in Dulbecco's modified Eagle medium (DMEM) containing 10% of foetal calf serum, at 37° C. in a humid environment containing 5% of $CO_2$. These cells are then cotransfected with an oncogenic Ras: Ha-ras Val12, plasmid psv2.ScFv.ras (see a) above) and a 10-fold excess of the neomycin resistance gene, by the cationic lipid transfection technique (Schweighoffer et al., Science, 256, 825–827, 1992). The same total amount of DNA is transfected for each dish.

24 hours after transfection, the transfected cells originating from each 100 mm Petri dish are divided in a ratio of 1 to 10 and cultured in the same medium but in the presence of G418 (GIBCO/BRL) at a concentration of 0.4 mg per ml of medium. The number of foci of transformation obtained per µg of transfected DNA is counted after 14 days of culture.

The results obtained are presented in the table below. They represent the mean of four independent tests.

| Transfected plasmids | Number of foci per µg of transfected DNA |
| --- | --- |
| Ha-Ras Val12 | 110 |
| psv2.ScFv.ras | 2 |
| Ha-Ras Val12 + psv2.ScFv.ras | 30 |

The results obtained show clearly that the intracellular anti-ras antibody very greatly decreases the transforming power of an oncogenic ras gene.

Moreover, in the light of the results obtained in a), expression of this ScFv fragment of Y13-159 antibody should also prevent transformation by other oncogenes such as HER1, HER2 facilitating the activation of cellular Ras proteins.

It is understood that a person skilled in the art can, on the basis of the results described in the present application, reproduce the invention with nucleic acid sequences coding for intracellular antibodies (such as ScFv fragments) directed against other cell components. These may be prepared either from known antibodies directed against cell components, or by identification of an antigen to be neutralized, immunization by means of this antigen or of a preferred epitope of the latter, and then preparation of the intracellular antibody from the antibody, its mRNA or hybridoma obtained. Other components involved in processes of cell transformation may thus be targeted. For example, other DNA sequences coding for intracellular anti-ras binding antibodies may be prepared according to the same methodology from M38, M8, M70, M90 and M30 (ATCC HB 9158) hybridomas, the antibodies of which are directed, respectively, against residues 1 to 23, 24 to 69, 90 to 106, 107 to 130 and 131 to 152 of the Ha-Ras protein. Furthermore, as mentioned above, vectors simultaneously carrying several sequences coding for different intracellular antibodies may advantageously be prepared in order to confer a superior neutralizing activity.

EXAMPLE 2

Cloning and expression of a DNA Sequence Coding for an Intracellular Anti-GAP Antibody This example describes the cloning and expression of a nucleic acid sequence coding for an intracellular binding protein reproducing the properties of a monoclonal antibody directed against GAP protein.

GAP protein (for GTPase Activating Protein) is involved in the ras-dependent signalling pathway. It interacts catalytically with ras proteins and multiplies 100- to 200-fold the rate of hydrolysis of GTP, measured in vitro for the normal p21 protein. Various studies have shown that the catalytic domain of this protein of approximately 1044 amino acids is located in the carboxy-terminal region (residues 702–1044), and that this region is reponsible for the interaction of GAP protein with the ras proteins (see W091/02,749).

It has now been shown that a monoclonal antibody directed against the so-called "SH3" domain of GAP protein neutralizes the functions of oncogenic Ras proteins in the Xenopus egg (Duchesne et al., Science, 259, 525–528, 1993).

According to the methodology described in 1.1., it is possible to synthesize a DNA sequence coding for an intracellular antibody (ScFv fragment) corresponding to this antibody (SEQ ID Nos. (3 and 4 ) residues 11 to 250, FIG. 1B). Such a sequence, incorporated in a vector, can enable the transforming power of an oncogenic ras gene in tumour cells to be inhibited.

Moreover, the Applicant has also identified more precisely the epitopes recognized by this antibody. These epitopes were then synthesized artificially, and may be used to generate new neutralizing antibodies capable of being used for carrying out the invention.

a) More precise identification:

The identification was carried out by the "epitope scanning" technique. This technique is based on the principle that a given antibody can react with peptides of 5 to 15 amino acids. As a result, the identification of sequential epitopes may be obtained by preparing a complete set of overlapping peptides, of 5–15 amino acids, corresponding to the complete sequence of the antigen in question. This technique was used to determine the functional epitopes of the "SH3" domain of GAP. To this end, the whole of this domain was explored by sequential overlaps, by synthesis of a decapeptide every other amino acid.

Synthesis of overlapping peptides 35 peptides covering the whole of the fragment of FIG. 1 were synthesized chemically. The synthesis was performed in duplicate, on 2 independent supports, by the Fmoc/t-butyl solid-phase method (Cambridge Research Biochemicals kit).

Detection of functional epitopes

The functional epitopes recognized by Ac200 antibody were visualized in an ELISA test with a peroxidase-coupled rabbit anti-mouse antibody. The chromogenic substrate used for the enzyme is aminobis(3-ethylbenzothiazodinesulphonate) (ABTS).

The results obtained show that the epitopes recognized by this antibody are as follows:

PVEDRRRVRAI (SEQ ID NO: 5)

EISF (SEQ ID NO: 6)

EDGWM (SEQ ID NO: 7)

These epitopes may be used according to the traditional techniques of a person skilled in the art to generate antibodies neutralizing the effects of ras. These antibodies or hybridomas producing them are then used to generate nucleic acid sequences and vectors of the invention, according to the methodology described above.

EXAMPLE 3

Preparation of a Nucleic Acid Sequence Coding for an Intracellular Anti-Ki-ras Antibody from mRNAs Extracted from Spleens of Mice Immunized with Peptides Derived from the Hypervariable Portions of Ki-Ras (2A and 2B)

This example describes the preparation of nucleic acid sequences coding for intracellular antibodies (such as ScFv fragments) according to the invention, by identification of an antigen to be neutralized, immunization by means of this antigen or of a preferred epitope of the latter, and then preparation of the nucleic acid sequence from the antibody, its mRNA or hybridoma obtained.

This example demonstrates the possibility of applying the present invention to any desired antigen or epitope, even when no monoclonal antibody directed against the said antigen or epitope is available.

The antigen targeted in this example is the Ki-ras protein. More precisely, the antigens used for the immunization are the peptides of 25 and 24 amino acids corresponding to the following terminal ends of the Ki-Ras 2A and 2B proteins:

Peptide 2A: (SEQ ID NO: 8) QYRLKKISKEEKTPGCVKIKKCIIM

Peptide 2B: (SEQ ID NO: 9) KYREKNSKDGKKKKKKSKTKCIIM

After immunization of mice with these peptides according to traditional techniques of immunology, the spleens are extracted and cDNAs are prepared from the mRNAs. The cDNAs coding for the variable regions are then cloned, leading to the formation of a library of phages expressing the ScFv fragments corresponding to the whole of the repertoire of the mice used. The intracellular antibodies (ScFv fragments) recognizing the peptides 2A and 2B are then identified and isolated by successive steps of selection on the basis of column and microtitration plate affinity tests.

These ScFv fragments are then tested functionally according to the protocol described in Example 1.

The strategy developed in this example makes it possible advantageously to select intracellular antibodies specific for the Ki-Ras oncogenes, which will hence not affect the other Ras proto-oncogenes. The selectivity of such tools is hence not only cellular (as a result of the uncoupling of the transduction pathways in Ras-transformed cells), but also molecular.

EXAMPLE 4

Preparation of a Nucleic Acid Sequence Coding for an Intracellular Anti-(mutated p53) Antibody This example describes the preparation of nucleic acid sequences coding for intracellular antibodies (such as ScFv fragments) directed against mutated p53 proteins. These intracellular antibodies are obtained from different monoclonal antibodies directed against the said mutated p53 proteins.

The gene coding for the p53 protein is altered in a very large number of tumour cells (Caron de Fromentel and Soussi, Genes, 4, 1–15, 1992). The mutated p53 protein does not have the same conformation as wild-type p53 (Lane and Benchimol, Genes Dev. 4, 1–8, 1990). This change in conformation may be detected by monoclonal antibodies (Milner and Cook, Virology, 154, 21–30, 1986; Milner, Nature, 310, 143–145, 1984).

pAB 240 antibodies recognize the mutated forms of the p53 proteins.

The intracellular expression of an ScFv fragment of antibodies specific for mutated p53 or of proteins interacting specifically with these mutated p53 proteins should induce a beneficial effect in tumours possessing a mutated p53.

EXAMPLE 5

Cloning and Expression of a DNA Sequence Coding for an Intracellular Anti-papillomavirus Antibody This example describes the cloning and expression of a DNA sequence coding for an intra-cellular antibody (ScFv fragment) directed against a protein of human papillomavirus (HPV).

The targeted viral protein is the E6 protein. This protein is produced by HPV 16 and 18 viruses, which are responsible for 90% of cancers of the cervix in women and have been identified in precancerous epithelial lesions (Riou et al., Lancet 335 (1990) 117). The E6 gene product leads to the formation of tumours by strongly decreasing the amount of wild-type p53, an anti-oncogene, in HPV-positive cells (Wrede et al., Mol. Carcinog. 4 (1991) 171). In other tumours, p53 is inhibited by different mechanisms: mutation (see Example 4) or combination with proteins such as MDM2.

The sequence of the E6 protein has been described in the literature (Hawley-Nelson et al., EMBO J. 8 (1989) 3905; Munger et al., J. Virol. 63 (1989) 4417). Particular regions of this protein may be identified by "epitope scanning" (see Example 2), and then used to immunize mice according to the protocol described in Example 3. The DNA sequence coding for the intracellular antibody (ScFv fragment) directed against the E6 protein of human papillomavirus (HPV) is then prepared according to the methodology described above. The functionality of this sequence is demonstrated after in vivo expression, by measuring:

the increase in the level of wild-type p53 in cells expressing E6, the morphological reversion of HPV-transformed cells, the blocking of the effects of E6 on the transactivation of p53, and the inhibition of the transformation by E6 of human keratinocytes and fibroblasts.

EXAMPLE 6

Preparation of a Nucleic Acid Sequence Coding for an Intracellular Anti-HIV Antibody from mRNAs Extracted from Spleens of Mice Immunized with Peptides Derived from Active Regions of the tat, rev and NCP7 Proteins This example describes the preparation of nucleic acid sequences coding for intracellular antibodies according to the invention (such as ScFv fragments), by identification of an antigen to be neutralized, immunization by means of this antigen or of a preferred epitope of the latter, and then preparation of the nucleic acid sequence from the antibody, its mRNA or hybridoma obtained.

This example further demonstrates the possibility of applying the present invention to any desired antigen or epitope, even when no monoclonal antibody directed against the said antigen or epitope has been described in the prior art.

The targeted antigens in this example are the tat, rev and NCP7 proteins of HIV virus. More precisely, the antigens used for the immunization are the following peptides of 6, 9 and 16 amino acids, corresponding to the regions of these proteins responsible for their interaction with mRNAs (in the case of tat and rev) or for the dimerization of RNAs (in the case of NCP7):

tat peptide: (SEQ ID NO: 10) RKKRRQRRR rev peptide: (SEQ ID NO: 11) RQARRNRRRRWR-ERQR NCP7 peptide: (SEQ ID NO: 12) RAPRKK After immunization of mice with these peptides according to conventional techniques of immunology, the spleens are extracted and cDNAs are prepared from the mRNAs. The cDNAs coding for the variable regions are then cloned, leading to the formation of a library of phages expressing the ScFv fragments corresponding to the whole of the repertoire of the mice used. The intracellular antibodies (ScFv fragments) recognizing the tat, rev and NCP7 peptides are then identified and isolated by successive steps of selection on the basis of column and microtitration plate affinity tests.

These ScFv fragments are then tested functionally for their capacity to block the replicative cycle of HIV virus.

What is claimed is:

1. An isolated nucleic acid comprising a gene coding for an intracellular single chain antibody specific for a ras oncogene under the control of a promoter wherein the antibody is functional in mammalian cells, as detected by inhibition of transformation of cells that express a ras oncogene.

2. The nucleic acid according to claim 1, wherein the single chain antibody has a binding site of a light-chain variable region of an antibody linked via a peptide linker to a binding site of a heavy-chain variable region of an antibody.

3. The nucleic acid according to claim 2 comprising a sequence as depicted in SEQ ID No. 1.

4. The nucleic acid according to claim 1, wherein the promoter is a viral promoter.

5. A vector comprising the nucleic acid of claim 1.

6. The vector according to claim 5 which is a viral vector.

7. The vector according to claim 5 further comprising a second nucleic acid encoding an Intracellular binding protein directed against a different epitope than the intracellular single chain antibody.

8. A pharmaceutical composition comprising a vector of claim 5 and a pharmaceutically acceptable carrier.

9. The pharmaceutical composition according to claim 8, formulated in liposomes or a complex with nuclear proteins, lipids or dextran.

10. The pharmaceutical composition according to claim 8, wherein the single chain antibody has a binding site of a light-chain variable region of an antibody linked via a peptide linker to a binding site of the heavy-chain variable region of an antibody.

11. The pharmaceutical composition according to claim 10, wherein the vector is a recombinant virus.

12. A replication defective recombinant virus comprising in its genome a nucleic acid according to claim 1.

13. The replication defective recombinant virus according to claim 12, which is an adenovirus.

14. A nucleic acid encoding the polypeptide comprising a sequence as depicted in SEQ ID No. 2.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 858 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..858

(ix) FEATURE:
        (A) NAME/KEY: misc_feature
        (B) LOCATION: 442..486
        (D) OTHER INFORMATION: /product= "Linker"

(ix) FEATURE:
        (A) NAME/KEY: misc_feature
        (B) LOCATION: 82..810
        (D) OTHER INFORMATION: /product= "ScFv anti-Ras"

(xi) SEQUENCE DESCRIPTION: SEQ ID NO:1:

```
TCA AGG AGA CAG TCT ATA AGA AAT ACC TAT TCG ACG GCA GCC GCT GGA        48
Ser Arg Arg Gln Ser Ile Arg Asn Thr Tyr Ser Thr Ala Ala Ala Gly
 1               5                  10                  15

TTG TTA TTA CTC GCG GCC CAG CCG GCC ATG GCT CAG GTG AAA CTG CAG        96
Leu Leu Leu Leu Ala Ala Gln Pro Ala Met Ala Gln Val Lys Leu Gln
             20                  25                  30

CAG TCA GGA GGA GGC TTA GTG CAG CCT GGA AGG TCC CTG AAA CTC TCC       144
Gln Ser Gly Gly Gly Leu Val Gln Pro Gly Arg Ser Leu Lys Leu Ser
         35                  40                  45

TGT GTA GTC TCT GGA TTC ACT TTC AGT AAC TAT GGA ATG AAC TGG ATT       192
Cys Val Val Ser Gly Phe Thr Phe Ser Asn Tyr Gly Met Asn Trp Ile
     50                  55                  60

CGC CAG ACT CCA GGG AAG GGA CTG GAG TGG GTT GCA TAC ATT AGT AGT       240
Arg Gln Thr Pro Gly Lys Gly Leu Glu Trp Val Ala Tyr Ile Ser Ser
```

-continued

```
              65                  70                  75                  80
GGT AGC AGT TAC CTC TAC TAT GCA GAA ACG GTG AAG GGC CGA TTC ACC        288
Gly Ser Ser Tyr Leu Tyr Tyr Ala Glu Thr Val Lys Gly Arg Phe Thr
                    85                  90                  95

ATC TCC AGA GAC AAT GCC AAG AAC ACC CTG TAC CTG CAA ATG ACC AGT        336
Ile Ser Arg Asp Asn Ala Lys Asn Thr Leu Tyr Leu Gln Met Thr Ser
            100                 105                 110

CTG AGG TCT GAA GAC ACT GCC TTG TAT TAC TGT GCA AGA CAT GAG GGT        384
Leu Arg Ser Glu Asp Thr Ala Leu Tyr Tyr Cys Ala Arg His Glu Gly
        115                 120                 125

ACG GGT ACC GAC TTC TTT GAT TAC TGG GGC CAA GGG ACC ACG GTC ACC        432
Thr Gly Thr Asp Phe Phe Asp Tyr Trp Gly Gln Gly Thr Thr Val Thr
    130                 135                 140

GTC TCC TCA GGT GGA GGC GGT TCA GGC GGA GGT GGC TCT GGC GGT GGC        480
Val Ser Ser Gly Gly Gly Gly Ser Gly Gly Gly Gly Ser Gly Gly Gly
145                 150                 155                 160

GGA TCG GAC GTT GAG CTC ACC CAG TCT CCA CAT TCC CTG TCT GCA TCT        528
Gly Ser Asp Val Glu Leu Thr Gln Ser Pro His Ser Leu Ser Ala Ser
                165                 170                 175

CTG GGA GAA ACT GTC TCC ATC GAA TGT CTA GCA AGT GAG GGC ATT TCC        576
Leu Gly Glu Thr Val Ser Ile Glu Cys Leu Ala Ser Glu Gly Ile Ser
            180                 185                 190

AAT TAT TTA GCG TGG TAT CAG CAG AAG CCA GGG AAA TCT CCT CAG CTC        624
Asn Tyr Leu Ala Trp Tyr Gln Gln Lys Pro Gly Lys Ser Pro Gln Leu
        195                 200                 205

CTG ATC TAT TAT GCA AGT AGC TTG CAG GAT GGG GTC CCA TCA CGG TTC        672
Leu Ile Tyr Tyr Ala Ser Ser Leu Gln Asp Gly Val Pro Ser Arg Phe
    210                 215                 220

AGT GGC AGT GGA TCT GGC ACA CAG TTT TCT CTC AAG ATC AGC AAC ATG        720
Ser Gly Ser Gly Ser Gly Thr Gln Phe Ser Leu Lys Ile Ser Asn Met
225                 230                 235                 240

CAA CCT GAA GAT GAA GGG GTT TAT TAC TGT CAA CAG GCT TAC AAG TAT        768
Gln Pro Glu Asp Glu Gly Val Tyr Tyr Cys Gln Gln Ala Tyr Lys Tyr
                245                 250                 255

CCT TCC ACG TTT GGA GCT GGC ACC AAG CTG GAA ATA AAA CGG GCG GCC        816
Pro Ser Thr Phe Gly Ala Gly Thr Lys Leu Glu Ile Lys Arg Ala Ala
            260                 265                 270

GCA GAA CAA AAA CTC ATC TCA GAA GAG GAT CTG AAT TAA TAA                858
Ala Glu Gln Lys Leu Ile Ser Glu Glu Asp Leu Asn  *   *
        275                 280                 285
```

(2) INFORMATION FOR SEQ ID NO:2:

(i) SEQUENCE CHARACTERISTICS:
        (A) LENGTH: 284 amino acids
        (B) TYPE: amino acid
        (D) TOPOLOGY: linear (ii) MOLECULE TYPE: protein (xi) SEQUENCE DESCRIPTION: SEQ ID NO:2:

```
Ser Arg Arg Gln Ser Ile Arg Asn Thr Tyr Ser Thr Ala Ala Ala Gly
 1               5                  10                  15

Leu Leu Leu Leu Ala Ala Gln Pro Ala Met Ala Gln Val Lys Leu Gln
            20                  25                  30

Gln Ser Gly Gly Gly Leu Val Gln Pro Gly Arg Ser Leu Lys Leu Ser
        35                  40                  45

Cys Val Val Ser Gly Phe Thr Phe Ser Asn Tyr Gly Met Asn Trp Ile
    50                  55                  60

Arg Gln Thr Pro Gly Lys Gly Leu Glu Trp Val Ala Tyr Ile Ser Ser
```

```
                65                  70                  75                  80
         Gly Ser Ser Tyr Leu Tyr Tyr Ala Glu Thr Val Lys Gly Arg Phe Thr
                             85                  90                  95

Ile Ser Arg Asp Asn Ala Lys Asn Thr Leu Tyr Leu Gln Met Thr Ser
                        100                 105                 110

Leu Arg Ser Glu Asp Thr Ala Leu Tyr Tyr Cys Ala Arg His Glu Gly
                    115                 120                 125

Thr Gly Thr Asp Phe Phe Asp Tyr Trp Gly Gln Gly Thr Thr Val Thr
                130                 135                 140

Val Ser Ser Gly Gly Gly Ser Gly Gly Gly Ser Gly Gly Gly
         145                 150                 155                 160

Gly Ser Asp Val Glu Leu Thr Gln Ser Pro His Ser Leu Ser Ala Ser
                        165                 170                 175

Leu Gly Glu Thr Val Ser Ile Glu Cys Leu Ala Ser Glu Gly Ile Ser
                        180                 185                 190

Asn Tyr Leu Ala Trp Tyr Gln Gln Lys Pro Gly Lys Ser Pro Gln Leu
                    195                 200                 205

Leu Ile Tyr Tyr Ala Ser Ser Leu Gln Asp Gly Val Pro Ser Arg Phe
                210                 215                 220

Ser Gly Ser Gly Ser Gly Thr Gln Phe Ser Leu Lys Ile Ser Asn Met
         225                 230                 235                 240

Gln Pro Glu Asp Glu Gly Val Tyr Tyr Cys Gln Gln Ala Tyr Lys Tyr
                        245                 250                 255

Pro Ser Thr Phe Gly Ala Gly Thr Lys Leu Glu Ile Lys Arg Ala Ala
                        260                 265                 270

Ala Glu Gln Lys Leu Ile Ser Glu Glu Asp Leu Asn
                    275                 280

(2) INFORMATION FOR SEQ ID NO:3:

(i) SEQUENCE CHARACTERISTICS:
        (A) LENGTH: 798 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..798

(ix) FEATURE:
        (A) NAME/KEY: misc_feature
        (B) LOCATION: 382..426
        (D) OTHER INFORMATION: /product= "Linker"

(ix) FEATURE:
        (A) NAME/KEY: misc_feature
        (B) LOCATION: 31..753
        (D) OTHER INFORMATION: /product= "ScFv anti-GAP"

(xi) SEQUENCE DESCRIPTION: SEQ ID NO:3:

TTA TTA CTC GCG GCC CAG CCG GCC ATG GCC CAG GTC CAA CTG CAG GAG     48
Leu Leu Leu Ala Ala Gln Pro Ala Met Ala Gln Val Gln Leu Gln Glu
         290                 295                 300

TCA GGA CCT GGC CTA GGG CAG CCC GCA CAG AGC ATT TCC ATA ACC TGC     96
Ser Gly Pro Gly Leu Gly Gln Pro Ala Gln Ser Ile Ser Ile Thr Cys
                305                 310                 315
```

```
ACA GTC TCT GGT TTC TCA TTA AGT AGC TAT GGT GTA CAC TGG GTT CGC      144
Thr Val Ser Gly Phe Ser Leu Ser Ser Tyr Gly Val His Trp Val Arg
        320                 325                 330

CAG TCT CCA GGA AAG GGT CTG GAG TGG CTG GGA GTG ATA TGG AGA GGT      192
Gln Ser Pro Gly Lys Gly Leu Glu Trp Leu Gly Val Ile Trp Arg Gly
335                 340                 345                 350

GGA GGC ACA GAC TAC AAT GCA GCC TTC ATG TCC AGA CTG AGC ATC ACC      240
Gly Gly Thr Asp Tyr Asn Ala Ala Phe Met Ser Arg Leu Ser Ile Thr
                355                 360                 365

AAG GAC AAC TCC AAG AGC CAA GTT TTC TTT AAA TTG AAC AGT CTG CAA      288
Lys Asp Asn Ser Lys Ser Gln Val Phe Phe Lys Leu Asn Ser Leu Gln
            370                 375                 380

CCT GAT GAC ACT GCC ATG TAC TAC TGT GCC AAA AGG GGT GGC CCG GGG      336
Pro Asp Asp Thr Ala Met Tyr Tyr Cys Ala Lys Arg Gly Gly Pro Gly
                385                 390                 395

TAT TTC GAT GTC TGG GGC CAA GGG ACC ACG GTC ACC GTC TCC TCA GGT      384
Tyr Phe Asp Val Trp Gly Gln Gly Thr Thr Val Thr Val Ser Ser Gly
        400                 405                 410

GGA GGC GGT TCA GGC GGA GGT GGC TCT AGC GGT GGC GGA TCG GAC ATT      432
Gly Gly Gly Ser Gly Gly Gly Gly Ser Ser Gly Gly Gly Ser Asp Ile
415                 420                 425                 430

GAG CTC ACC CAG TCT CCA GCC TCC CTA TCT GCA TCT GTG GGA GAA ACT      480
Glu Leu Thr Gln Ser Pro Ala Ser Leu Ser Ala Ser Val Gly Glu Thr
                435                 440                 445

GTC ACC ATG ACA TGT CGA GCA AGT GAG AAT ATT TAC AGT AAT TTA GCA      528
Val Thr Met Thr Cys Arg Ala Ser Glu Asn Ile Tyr Ser Asn Leu Ala
            450                 455                 460

TGG TAT CAG CAG AAA CAG GGA AAG TCT CCT CAG CTC CTG GTC TAT GCT      576
Trp Tyr Gln Gln Lys Gln Gly Lys Ser Pro Gln Leu Leu Val Tyr Ala
                465                 470                 475

GCA ACA AAA CCA GGA AAT GGT GTG CCA TCA AGG TTC AGT GGC AGT GGA      624
Ala Thr Lys Pro Gly Asn Gly Val Pro Ser Arg Phe Ser Gly Ser Gly
480                 485                 490

TCA GGC ACA CAA TTT TCT CTG AAG ATC AAC AGC CTG CAG CCT GAA GAT      672
Ser Gly Thr Gln Phe Ser Leu Lys Ile Asn Ser Leu Gln Pro Glu Asp
495                 500                 505                 510

CTT GGG AAC TAT TAC TGT CTA CAT TTT TAT GGG ACT CCG TAT AGG TTC      720
Leu Gly Asn Tyr Tyr Cys Leu His Phe Tyr Gly Thr Pro Tyr Arg Phe
                515                 520                 525

GGC GGG GGC ACC AAG CTG GAA ACG AAA CGG GCG GCC GCA GAA CAA AAA      768
Gly Gly Gly Thr Lys Leu Glu Thr Lys Arg Ala Ala Ala Glu Gln Lys
            530                 535                 540

CTC ATC TCA GAA GAG GAT CTG AAT TAA TAA                              798
Leu Ile Ser Glu Glu Asp Leu Asn *   *
            545                 550
```

(2) INFORMATION FOR SEQ ID NO:4:

(i) SEQUENCE CHARACTERISTICS:
        (A) LENGTH: 264 amino acids
        (B) TYPE: amino acid
        (D) TOPOLOGY: linear (ii) MOLECULE TYPE: protein (xi) SEQUENCE DESCRIPTION: SEQ ID NO:4:

```
Leu Leu Leu Ala Ala Gln Pro Ala Met Ala Gln Val Gln Leu Gln Glu
1               5                   10                  15

Ser Gly Pro Gly Leu Gly Gln Pro Ala Gln Ser Ile Ser Ile Thr Cys
            20                  25                  30
```

```
Thr Val Ser Gly Phe Ser Leu Ser Ser Tyr Gly Val His Trp Val Arg
            35                  40                  45

Gln Ser Pro Gly Lys Gly Leu Glu Trp Leu Gly Val Ile Trp Arg Gly
        50                  55                  60

Gly Gly Thr Asp Tyr Asn Ala Ala Phe Met Ser Arg Leu Ser Ile Thr
65                  70                  75                  80

Lys Asp Asn Ser Lys Ser Gln Val Phe Phe Lys Leu Asn Ser Leu Gln
                85                  90                  95

Pro Asp Asp Thr Ala Met Tyr Tyr Cys Ala Lys Arg Gly Gly Pro Gly
            100                 105                 110

Tyr Phe Asp Val Trp Gly Gln Gly Thr Thr Val Thr Val Ser Ser Gly
        115                 120                 125

Gly Gly Ser Gly Gly Gly Gly Ser Ser Gly Gly Gly Ser Asp Ile
130                 135                 140

Glu Leu Thr Gln Ser Pro Ala Ser Leu Ser Ala Ser Val Gly Glu Thr
145                 150                 155                 160

Val Thr Met Thr Cys Arg Ala Ser Glu Asn Ile Tyr Ser Asn Leu Ala
            165                 170                 175

Trp Tyr Gln Gln Lys Gln Gly Lys Ser Pro Gln Leu Leu Val Tyr Ala
        180                 185                 190

Ala Thr Lys Pro Gly Asn Gly Val Pro Ser Arg Phe Ser Gly Ser Gly
        195                 200                 205

Ser Gly Thr Gln Phe Ser Leu Lys Ile Asn Ser Leu Gln Pro Glu Asp
210                 215                 220

Leu Gly Asn Tyr Tyr Cys Leu His Phe Tyr Gly Thr Pro Tyr Arg Phe
225                 230                 235                 240

Gly Gly Gly Thr Lys Leu Glu Thr Lys Arg Ala Ala Glu Gln Lys
            245                 250                 255

Leu Ile Ser Glu Glu Asp Leu Asn
            260

(2) INFORMATION FOR SEQ ID NO:5:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Pro Val Glu Asp Arg Arg Val Arg Ala Ile
1               5                   10

(2) INFORMATION FOR SEQ ID NO:6:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Glu Ile Ser Phe
1

(2) INFORMATION FOR SEQ ID NO:7:
```

```
        (i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Glu Asp Gly Trp Met
1               5

(2) INFORMATION FOR SEQ ID NO:8:

(i) SEQUENCE CHARACTERISTICS:
            (A) LENGTH: 25 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Gln Tyr Arg Leu Lys Lys Ile Ser Lys Glu Glu Lys Thr Pro Gly Cys
1               5                  10                  15

Val Lys Ile Lys Lys Cys Ile Ile Met
            20                  25

(2) INFORMATION FOR SEQ ID NO:9:

(i) SEQUENCE CHARACTERISTICS:
            (A) LENGTH: 24 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Lys Tyr Arg Glu Lys Asn Ser Lys Asp Gly Lys Lys Lys Lys Lys Lys
1               5                  10                  15

Ser Lys Thr Lys Cys Ile Ile Met
            20

(2) INFORMATION FOR SEQ ID NO:10:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:10:

Arg Lys Lys Arg Arg Gln Arg Arg Arg
1               5

(2) INFORMATION FOR SEQ ID NO:11:

(i) SEQUENCE CHARACTERISTICS:
            (A) LENGTH: 16 amino acids
            (B) TYPE: amino acid
            (C) STRANDEDNESS:
            (D) TOPOLOGY: linear (ii) MOLECULE TYPE: peptide
```

(xi) SEQUENCE DESCRIPTION: SEQ ID NO:11:

Arg Gln Ala Arg Arg Asn Arg Arg Arg Trp Arg Glu Arg Gln Arg
1               5                   10                  15

(2) INFORMATION FOR SEQ ID NO:12:

(i) SEQUENCE CHARACTERISTICS:
         (A) LENGTH: 6 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:12:

Arg Ala Pro Arg Lys Lys
1               5

(2) INFORMATION FOR SEQ ID NO:13:

(i) SEQUENCE CHARACTERISTICS:
         (A) LENGTH: 7 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:13:

Met Pro Lys Lys Lys Arg Lys
1               5

(2) INFORMATION FOR SEQ ID NO:14:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (ix) FEATURE:
         (A) NAME/KEY: CDS
         (B) LOCATION: 1..12

(xi) SEQUENCE DESCRIPTION: SEQ ID NO:14:

GAA TTC ACT GGC                                              12
Glu Phe Thr Gly
            270

(2) INFORMATION FOR SEQ ID NO:15:

(i) SEQUENCE CHARACTERISTICS:
         (A) LENGTH: 4 amino acids
         (B) TYPE: amino acid
         (D) TOPOLOGY: linear (ii) MOLECULE TYPE: protein (xi) SEQUENCE DESCRIPTION: SEQ ID NO:15:

Glu Phe Thr Gly
  1

(2) INFORMATION FOR SEQ ID NO:16:

```
    (i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..12

(xi) SEQUENCE DESCRIPTION: SEQ ID NO:16:

GAA TTC ACT GGC                                                              12
Glu Phe Thr Gly
  5

(2) INFORMATION FOR SEQ ID NO:17:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:17:

Glu Phe Thr Gly
```